United States Patent
Markussen et al.

(10) Patent No.: US 10,662,403 B2
(45) Date of Patent: May 26, 2020

(54) METHOD AND APPARATUS FOR ATTACHING, DETECTING AND RETRIEVING A SINGLE CELL ON A SURFACE

(71) Applicant: CytoTrack ApS, Lyngby (DK)

(72) Inventors: Tom Hede Markussen, Bagsværd (DK); Lars Ulrik Nielsen, Virum (DK); Robert Naumovski, Malmö (SE); Anders Skærlund Frandsen, Ølsted (DK); Henrik Stender, Gentofte (DK)

(73) Assignee: CytoTrack ApS, Lyngby (DK)

( * ) Notice: Subject to any disclaimer, the term of this patent is extended or adjusted under 35 U.S.C. 154(b) by 113 days.

(21) Appl. No.: 15/560,700

(22) PCT Filed: Mar. 21, 2016

(86) PCT No.: PCT/DK2016/050084
§ 371 (c)(1),
(2) Date: Sep. 22, 2017

(87) PCT Pub. No.: WO2016/150446
PCT Pub. Date: Sep. 29, 2016

(65) Prior Publication Data
US 2018/0119086 A1    May 3, 2018

(30) Foreign Application Priority Data

Mar. 24, 2015   (DK) .................................. 2015 70168

(51) Int. Cl.
| | | |
|---|---|---|
| *C12M 1/00* | (2006.01) | |
| *C12M 1/26* | (2006.01) | |
| *G01N 15/14* | (2006.01) | |
| *G01N 1/28* | (2006.01) | |

(52) U.S. Cl.
CPC ............ *C12M 47/04* (2013.01); *C12M 33/04* (2013.01); *G01N 1/28* (2013.01); *G01N 1/2813* (2013.01); *G01N 15/1468* (2013.01); *C12M 33/10* (2013.01); *C12M 47/14* (2013.01)

(58) Field of Classification Search
None
See application file for complete search history.

(56) References Cited

U.S. PATENT DOCUMENTS

| | | | | |
|---|---|---|---|---|
| 8,362,446 B1* | 1/2013 | Caspersen | .......... | G01N 15/1468 |
| | | | | 250/458.1 |
| 2012/0225475 A1* | 9/2012 | Wagner | .................. | G01N 15/14 |
| | | | | 435/288.7 |
| 2014/0065637 A1* | 3/2014 | Kirk | .................... | G01N 15/1463 |
| | | | | 435/7.1 |

FOREIGN PATENT DOCUMENTS

| | | |
|---|---|---|
| DE | 19714987 C1 | 9/1998 |
| WO | WO 03/023354 A2 | 3/2003 |

OTHER PUBLICATIONS

Machine translation of DE19714987 published Sep. 24, 1998.
Karsten, S.L. et al, "Collection and clonal expansion of individual cells from adherent cultures with KuiqpickTM"; NEUROINDX Application Note #3; pp. 1-4, 2013.
Ma, Z. et al, KuiqpicKTM: A Novel Instrument for Rapid Collection of Individual Live Cells from adherent Cutures; ABRF 2014 Journal of Biomolecular Techniques, vol. 25, Supplement, May 2014, p. S25.
Zeng, Jia et al, "A Minimally Invasive Method for Retrieving Single Adherent Cells of Different Types from Cultures," Scientific Reports 4:5424; Jun. 24, 2014.

* cited by examiner

*Primary Examiner* — Nghi V Nguyen
(74) *Attorney, Agent, or Firm* — Dinsmore & Shohl LLP; Weston R. Gould

(57) ABSTRACT

The present disclosure relates to a method for attaching, detecting and retrieving a single cell on a manipulation medium comprising the steps of: attaching the single cell onto the manipulation medium by applying a carrier liquid; partially drying out the carrier liquid; detecting a property of the single cell by rotating the manipulation medium and scanning a light beam over the manipulation medium; loosening the single cell from the manipulation medium without damaging the single cell by manipulating the single cell with an instrument; and retrieving the single cell from the manipulation medium by aspirating the single cell into a tube, wherein the carrier liquid is dried out to a degree corresponding to that the single cell does not move during the rotation of the manipulation medium and that the single cell can be loosened by the instrument without damaging the single cell. The disclosure further relates to an apparatus for detection and manipulation of one or more object(s).

12 Claims, 3 Drawing Sheets

METHOD AND APPARATUS FOR ATTACHING, DETECTING AND RETRIEVING A SINGLE CELL ON A SURFACE

The present disclosure relates to a method for attaching, detecting and retrieving a single cell on a manipulation medium and an apparatus for detection and manipulation of one or more objects.

BACKGROUND OF INVENTION

The field of single cell analysis has grown considerably in the last decade. Typically, the existing methods for single cell analysis require isolation of the single cell.

U.S. Pat. No. 8,362,446 describes an apparatus which can perform an optical scanning of a biological mass (e.g. a blood sample) and identify rare objects (such as, e.g., circulating cancer cells or any single cell). The blood sample is placed on a glass disc in a single layer (monolayer) in which they are attached to the surface through chemical bonds. During the scanning, the glass disc is rotated. By use of such a system it would be beneficial to be able to lift such selected objects (e.g. circulating cancer cells) from the disc into a container or another system. This container or system will make it possible to subject the object to further analysis or characterization, e.g. relating to DNA, mRNA or genes.

One problem with such systems is that it is typically difficult to loosen them from the surface without damaging them. A typical procedure is to scrape them off from the surface mechanically whereby they normally integrate and the structure becomes damaged. This damage is often problematic and destructive to the further characterization. When cells are scraped off from a surface, they will often disintegrate (crumble), thus increasing the likelihood of obtaining mixed material from other cells. Certain properties of a cell, such as, e.g., mRNA, are very delicate and will be very easily damaged if the cell disintegrates.

There are various methods/systems on the market which are developed for lifting cells from a glass surface. The best known are called laser manipulation (laser micro manipulation). Here laser light is used on the one hand for cutting cells from a tissue section and on the other hand for lifting and transporting the isolated cell from the surface and into a container. These systems may be designed in two ways. (1) The cells are placed directly on the glass, and the laser light releases the cell from the surface through the supply of heat. (2) A thin membrane is placed on top of the glass on which the cells are attached. Here the laser light is used both for cutting out the membrane and for lifting up the cell which is still stuck to the membrane and placing it into a container. The laser is typically placed beneath the glass surface, and the direction of the laser light lifts the cell upwards. A substantial problem with these laser-based systems is that they are very expensive and complex to use.

The apparatus described in U.S. Pat. No. 8,362,446 is normally used for blood cells, which, contrary to tissue cells, are normally loose individuals. When it is desired to lift selected cells from the surface, it will normally not be necessary to cut the individual cell from a coherent tissue of cells (tissue section). It is only necessary to release the cell from the surface.

DE patent No. 19714987 C1 describes an instrument for collecting cells from a glass surface. This instrument uses a combination of a steel capillary and a concentric glass capillary. The steel capillary is designed to scrape a cell off the medium. This scraping function will often destroy the integrity of the cell because the cell is at the same time stuck firmly to the surface.

SUMMARY OF INVENTION

The present disclosure relates to a method for attaching, detecting and retrieving a single cell on a manipulation medium comprising the steps of:
attaching the single cell onto the manipulation medium by applying a carrier liquid;
partially drying out the carrier liquid;
detecting a property of the single cell by rotating the manipulation medium and scanning a light beam over the manipulation medium;
loosening the single cell from the manipulation medium without damaging the single cell by manipulating the single cell with an instrument; and
retrieving the single cell from the manipulation medium by aspirating the single cell into a tube,
wherein the carrier liquid is dried out to a degree corresponding to that the single cell does not move during the rotation of the manipulation medium and that the single cell can be loosened by the instrument without damaging the single cell.

Since the scanning process involves rotation of the manipulation medium (preferably a surface, typically some kind of disc, such as a glass disc), the cells need to be attached to the surface so that they do not fall off due to centrifugal forces when the disc is rotated. One method that is used to make the cells adhere to the manipulation medium is to distribute a smearing liquid and let the liquid and cells dry. In the present disclosure, the inventors use the fact that during the rotation of the manipulation medium there is a threshold of adhesion of the cells for sticking to the manipulation medium such that the cells do not move when the manipulation medium is rotated at a predefined speed. Therefore, the carrier liquid is only partially dried out i.e. the process of drying the carrier liquid is stopped at some point when the carrier liquid has dried to a degree corresponding to that the single cell does not move during the rotation of the manipulation medium. The drying process is stopped at a point where the cells are not completely adhered, such that they can be loosened by the instrument without damaging the single cell. Preferably, the detected single cell is then gently loosened from the manipulation medium by means of an instrument such as by the tip of an instrument, such as a tube. Since the single cell is only adhered to a level corresponding to that the single cell does not move during the rotation of the manipulation medium, the instrument may be moved in a controlled manner to push or rub the single cell loose without damaging the single cell.

When the single cell is removed from the surface, it may be acceptable that the cell is slightly deformed as long as the cell is intact i.e. the cell membrane is not broken.

The present disclosure further relates to an apparatus for detection and manipulation of one or more object(s), the apparatus comprising:
a micromanipulation system comprising a control unit, an arm adapted for holding a tube, optionally adapted for holding the tube via one or more tube clamps, wherein the tube is adapted to loosen the object(s), and in which the tube is adapted to be moved in one or more directions following instructions from the control unit,
a microscope having a field of view, said field of view comprising at least one manipulation level where the object(s) is/are situated and the field of view being adapted such that the object(s) and the tube can be in the field of view at the same time.

The apparatus may be used for carrying out the presently disclosed method for attaching, detecting and retrieving a single cell on a manipulation medium. The tube may be adapted to push and/or rub the object loose. The apparatus may thereby further comprise means for applying a carrier liquid to a manipulation medium on which the object is placed; scanning and rotation means; and a control unit, preferably comprising processing means for calculating and/or analyzing the drying level of carrier liquid and/or the level of adhesion of the object(s).

DETAILED DESCRIPTION OF THE INVENTION

Figure 1:
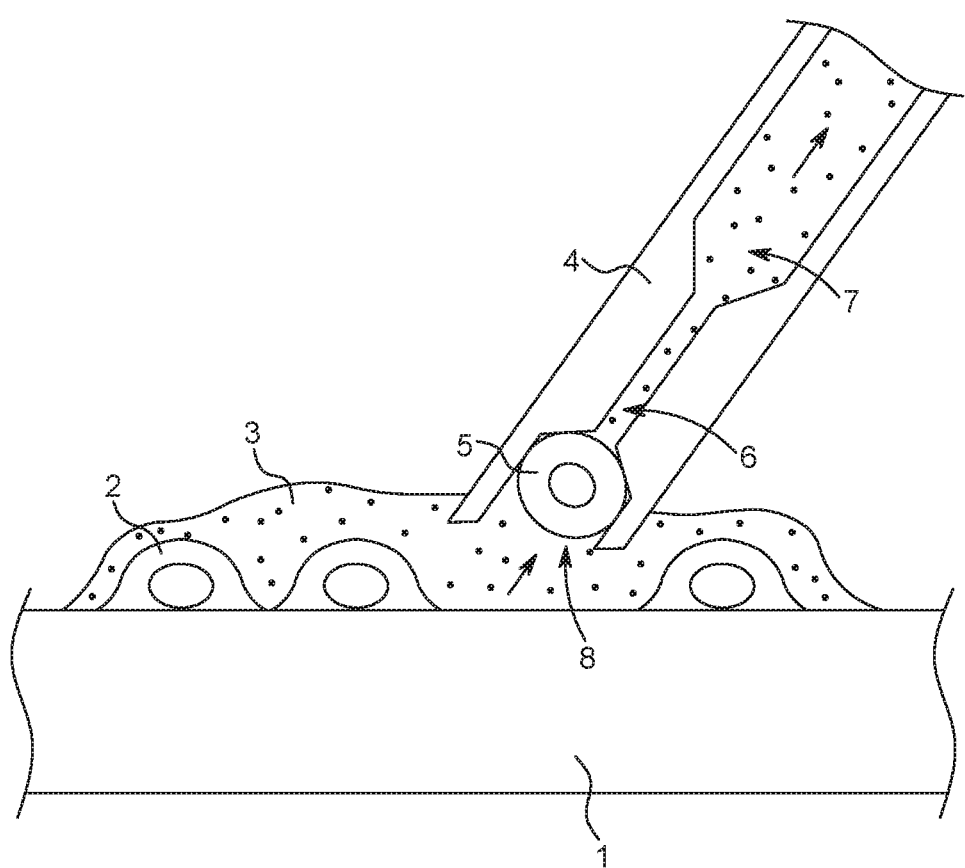
FIG. 1 shows one embodiment of a tube for aspirating a single cell. The tube may also be used to loosen a single cell from a manipulation medium.

As stated, the present disclosure relates to a method for attaching, detecting and retrieving a single cell on a manipulation medium comprising the steps of:
  attaching the single cell onto the manipulation medium by applying a carrier liquid;
  partially drying out the carrier liquid;
  detecting a property of the single cell by rotating the manipulation medium and scanning a light beam over the manipulation medium;
  loosening the single cell from the manipulation medium without damaging and/or breaking the single cell by manipulating the single cell with an instrument; and
  retrieving the single cell from the manipulation medium by aspirating the single cell into a tube,
  wherein the carrier liquid is dried out to a degree corresponding to that the single cell does not move during the rotation of the manipulation medium and that the single cell can be loosened by the instrument without damaging and/or breaking the single cell.

Since the scanning process involves rotation of the manipulation medium (preferably a surface, typically some kind of disc, such as a glass disc), the cells need to be attached to the surface so that they do not fall off due to centrifugal forces when the disc is rotated. One method that is used to make the cells adhere to the manipulation medium is to distribute a smearing liquid and let the liquid and cells dry. In the present disclosure, the inventors use the fact that during the rotation of the manipulation medium there is a threshold of adhesion of the cells for sticking to the manipulation medium such that the cells do not move when the manipulation medium is rotated at a predefined speed.

In the attachment process, one method involves cytospin. In cytospins, single cell suspensions are spun onto a surface by use of a cytocentrifuge. A cytocentrifuge spins cells at an angle, at low speeds, and accelerates and decelerates gradually. The fluid from the suspension may be absorbed onto filter paper while the centrifuge is spinning. This allows the cells to adhere to the surface in a monolayer format. This represent an efficient process for attaching the cells quickly. In the presently disclosed method, the cells may alternatively be attached by distribution of a smearing liquid, which may be beneficial for the subsequent step of retrieving a single cell.

Preferably a balance is created between the fact that the cells are sufficiently stuck on the surface so that they do not lose their position on the disc during the various procedural steps which normally take place during and after the scanning itself (e.g. g-forces during rotating scanning), and the fact that they are sufficiently loose so that they can subsequently be pushed to be released individually and intact from the surface (without disintegrating). A parameter that may also be taken into account as part of the balancing is the speed at which the disc is rotated, which influences the forces on the cells. In the rotation process, the single cell may be exposed to centrifugal forces, translational forces or gravitational forces.

Therefore, the carrier liquid is only partially dried out i.e. the process of drying the carrier liquid is stopped at some point when the carrier liquid has dried to a degree corresponding to that the single cell does not move during the rotation of the manipulation medium. The drying process is stopped at a point where the cells are not completely adhered, such that they can be loosened by the instrument without damaging the single cell. Preferably, the detected single cell is then gently loosened from the manipulation medium by means of an instrument such as by the tip of a tube. Since the single cell is only adhered to a level corresponding to that the single cell does not move during the rotation of the manipulation medium, the instrument may be moved in a controlled manner to push or rub the single cell loose without damaging the single cell.

In one embodiment the manipulation medium is a surface, such as a glass surface. The surface may be characterized in that the material of which it is made comprises glass coated with a coating that binds the cells to the surface, either through chemical bonds and/or by an electric charge. Normal commercial coating such as, e.g., Poly-L-Lysin or SuperFrost or the like ensures that the cells are attached to the surface. In the present disclosure such coatings may be used but contrary to normal laboratory practice, the cells are preferably only partially dried out. In one embodiment the coating is selected from the group of Poly-L-Lysin or SuperFrost.

In one embodiment, referring to the presently disclosed method for attaching, detecting and retrieving an object, the method performs the following steps:
  1. Place an object or several objects (e.g. a cell or a microorganism) on a surface.
  2. Attach the object(s) on the surface so that it/they is/are retained to a sufficient degree so that they do not move during an analytical process (e.g. an optical scanning).
  3. Analyse the objects during a scanning process, the objects attached to the surface being subjected to centrifugal forces, translational forces, gravitational forces, and wherein they are retained to such a degree that they do not move on the surface.
  4. Release and lift the object(s) from the surface without damaging the basic integrity of the object(s).
  5. Position the object(s) on the same surface or on another surface or in a container (e.g. an Eppendorf tube) with the purpose that the object may subsequently be further analysed and characterized (e.g. by PCR [Polymerase Chain Reaction] or NGS [Next-Generation Sequencing] technologies).

In the method according to the present disclosure, scraping the cells loose is not necessarily needed as the cells are attached with looser bonds so that it is easier to loosen the cells, for example by pushing or rubbing them loose.

In one embodiment of the presently disclosed method, the liquid is spread with the cells by a common smear. The cells are preferably not dried out completely as is typically done in the case of a smear. The cells are preferably only dried out to a degree so that only the carrier liquid has visibly evaporated.

When the carrier liquid has evaporated, there are at least two possibilities. Either a layer of a protective liquid is poured over the cells (mounting medium) which are then covered by a cover glass, or the disc is alternatively placed uncovered in a container. The container may ensure that the cells do not dry out completely.

As described in U.S. Pat. No. 8,362,446 the disc may be rotated with a high rotational speed (up to 1000 RPM) in the scanning process. By this scanning, it is preferred that the cells on the disc do not move on the surface of the disc. A normal working procedure is that certain positions on the disc where interesting events have been detected will be searched. The cells must therefore be sufficiently stuck so that they do not lose their position during rotation, including g-forces from the rotation.

An apparatus for detecting a property of marked objects in a specimen has been disclosed in U.S. Pat. No. 8,362,446, the apparatus comprising a frame, a member positioned on the frame and having a surface that is adapted to receive and hold the specimen, a light source for emission of a light beam towards the specimen held by the member, a detector for detection of light emitted from marked objects upon interaction with the light beam said light source and said detector being arranged so that a part of a light beam path from the light source to the specimen isco-axial with a part of the light emitted from the marked objects towards the detector, scanning means for scanning the specimen in relation to the detector along a non-linear curve, scanning control means for controlling the scanning means for scanning the specimen along a predetermined curve, characterised in that the apparatus comprises storage means for storage of signals relating to the detected objects provided by the detector and corresponding position signals provided by the scanning control means, means for retrieving position signals stored in the storage means, and a microscope for optical inspection of detected objects, in that the scanning means comprises means for rotating the member and means for displacing the member along a radius of the rotation of the member, so as to detect the property of marked objects in the entire specimen, and in that the scanning control means are adapted to place the microscope at the position of any detected object.

An apparatus having these features may be used in the present invention for the step of detecting a property of the single cell by rotating the manipulation medium and scanning a light beam over the manipulation medium.

In the cases where a mounting medium and cover glass are used, it is preferred that the cells are sufficiently stuck so that when the cover glass and the mounting medium are subsequently removed/washed off, the cells remain stuck to the surface without changing their position or fall off. If the cells remain at their positions it is subsequently possible to retrieve the cells which have been selected by the primary scanning and which are to be characterized further, e.g. by lifting them from the surface and remove them to another apparatus which can characterize the individual cell(s).

The surface will normally be characterized in that the basic material consists of glass coated with a coating that binds the cells to the surface, either through chemical bonds and/or by an electric charge. Normal commercial coating such as, e.g., Poly-L-Lysin or SuperFrost or the like, may ensure that the cells are well attached to the surface. In the method according to the present disclosure, such coatings may also be used, but contrary to normal laboratory practice, the cells are only partially dried out. In normal laboratory practice, cells are normally dried out completely, e.g. by a long drying time, heating (in an incubator or an oven) or by flame drying, and/or chemically by spraying/layering alcohol or acetone or other means onto the cells which are subsequently dried, thus dehydrating liquid in the cells, and the cells will stick very well. Afterwards, when the cells are to be loosened from the surface, a small volume of liquid may be placed in an area on or around the cell or layered over the cell. The liquid may be e.g. water, an oil, PBS, any buffer or another liquid. This liquid may dissolve most of the bonds fixing the cells, however typically not to a degree that the cells float around. The cell may absorb at least a part of the liquid, which may assist the process of loosening the cell from the surface. Now a thin tube (e.g. a capillary or a micro pipette) may be used to push/rub the individual cell free from the surface. The tube is either placed at an angle or orthogonally to the surface. The tube is preferably moved by means of micromanipulation equipment which can move the tube a few micrometres at a time. The purpose of these small movements is to loosen the cell from the surface without substantially breaking or damaging the cell. The cell is pushed in a controlled manner a few micrometres at a time. Even though the selected cell is placed close to other cells ("shoulder by shoulder"), it is possible to move only the selected cell.

However, the surrounding cells may also be moved at the same time. This means that some of the neighbouring cells may also be unintentionally released. However, in a preferred embodiment the collection is restricted to the selected cell only. In the case where unselected cells are included, these may be sorted out in a subsequent process step.

During this pushing process, the operator is preferably able to observe the process as long as the movement of the tube is controlled manually by the operator. Typically this process takes place under the microscope where the operator can follow live where the process takes place. However, the process can also be automated such that the process is monitored by a vision system and where the movement of the tube is controlled by a robot. This process can either be semiautomatic or fully automatic. In the apparatus described in U.S. Pat. No. 8,362,446, the system holding and moving the tube can be placed and integrated such that the tube is placed directly under the microscope. Thus, it may not be necessary to make a separate dedicated detection system for cell collection. Preferably the operator is able to see the cell(s) to be collected, but at the same time also see the surrounding cells which should preferably not be collected.

In the apparatus described in U.S. Pat. No. 8,362,446, all cells are normally fluorescently marked. The operator can therefore see the cells through the fluorescence microscope. It will also be possible to use an ordinary light microscope which does not detect fluorescence. By use of the fluorescence microscope it will be advantageous to use a filter which is open in several colour bands so that the operator can recognize certain colours and thus certain cells so that it is possible to make a distinction between the cells to be collected and the cells not to be collected.

The tube used for pushing the cells may also be used for aspirating the cells. In principle, it may be two different devices, but it is advantageous that the tube be used for both purposes as only one system is to be controlled and only one manipulation system is necessary. The tube may be filled with a liquid, e.g. oil or water or another sort of carrier medium. When the operator has loosened the cell from the surface by pushing it, the opening of the tube is moved near the cell, and a pump aspirates the cell into the tube. In one embodiment the pump is capable of aspirating a very small amount of liquid at a time so that the cell will only just be lifted up into the tube. This ensures that the cell does not disappear into the pump system, but that it remains at the start of the tube. When the operator subsequently reverses the pump, it will be easy for the cell to come out of the tube again.

When the cell is aspirated into the tube, some undesired cells may sometimes be included. This may typically occur when the cell to be isolated is located adjacent to or even abutting other cells. In this scenario the single cell and the unintentionally aspirated cells may be released from the tube onto a manipulation medium, such as a glass surface, preferably by spreading the cells on a larger area, where the single cell can be more easily be collected. The cells may be distributed on a new surface. New smear of the cells (if necessary onto a larger area) will often make it possible to aspirate the desired cell again without including the undesired neighbours. Alternatively, it may be acceptable in some cases that a few undesired neighbouring cells are included, depending on the purity requirements of the subsequent process(es).

When the desired cell has been isolated and is present in the tube in the carrier liquid within the pump system, it can be transferred either to a container (e.g. an Eppendorf tube) or to another surface (e.g. a microscope slide) or to the same surface (glass disc), but in a position where there is free space.

The tube is lifted away from the disc and into the position where it is desired to place the cell. Alternatively, the tube is lifted up and the glass disc is removed, and the new surface is advanced under the tube. The tube can also be retained permanently, and the other elements moved relative to the tube. In one embodiment of the invention, the tube is lifted up and the linear slide holding the glass disc is moved. The new element, to which it is desired to transfer the cell, emerges under the tube as it is also mounted to the same slide. The tube is then lowered and the cell is pumped onto the surface or into the container together with the carrier liquid. By coupling the new surface (e.g. a microscope slide) or the container to the same slide, a mechanically simpler and cheaper system is obtained with fewer movements. Another advantage is that the microscope is placed above the cell and the opening of the tube during the entire procedure. Thus, it is possible for the operator to monitor the cell continuously during all process steps.

The present method and apparatus may be regarded as a combination of individually controlled processes which, taken together, make it possible to obtain a desired effect.

By attaching the single cell onto the manipulation medium by applying a carrier liquid; partially drying out the carrier liquid; then scanning cells with the non-linear scanning principle described in U.S. Pat. No. 8,362,446 involving rotation of the surface, and then relatively easily isolating a certain selected cell for a medium (slide or container) so that this selected cell can be transferred to other characterization systems, such as single cell PCR, an efficient an precise system for analysing and retrieving cells is achieved.

The individually controlled processes may in this respect be: laying out and attachment to the glass disc, retaining during various scanning and characterization processes on the glass disc, loosening in basic intact form and transfer to a medium suitable for further characterization. The basis for the method for cell isolation is that the cell mass (e.g. a blood sample) has been kept in a test tube or a tube. The cell mass may be subject to processes in which the cell mass is cleaned of elements that are not relevant for the analysis, which can be removed relatively easily with common methods (e.g. red blood cells and serum). This may be carried out e.g. by centrifugation, pipetting of layers (e.g. "buffy coat" isolation), rinsing processes, and/or lysing processes. In one embodiment of the process, lysis and fixation is performed after the step of "buffy coat" isolation/separation. Preferably, a lysis buffer comprising a fixation medium is used. In the lysis (and optionally fixation) step, rests of red blood cells after the step of "buffy coat" isolation/separation are subject to lysis. After these process steps, the size of the biological mass may be reduced, and it is then relatively easy to identify the specific elements to be analysed.

After the lysis and fixation, the cells may undergo a labelling process in which the cells which are to be to identified are coloured/stained with fluorescence markers (e.g. an antibody to cytokeratin or EpCAM). The staining of the cells preferably takes place before the cells are placed on the surface for the scanning and detection process. These processes are common and are e.g. used in connection with flow cytometry. At the end of the labelling process, all the cells are situated in a carrier liquid such as, e.g., water or PBS.

After the labelling process, the liquid with the cell mass which e.g. consists of 100 million cells is spread over a glass disc. This can be done with a smearing technique in which one or more drops laid out on the surface is/are smeared with a scraper ("smearing"). This scraper is typically made from a liquid-repellent material so that no cells or only very few cells are left on the scraper. The liquid with the cells are now evenly distributed over the surface, and during the evaporation process the cells drop down on the surface partly because of the gravitational force, partly because the carrier liquid gradually disappears. When the carrier liquid has evaporated, almost all cells will have landed on the surface and they gradually start to attach to the surface. The attachment is increased as the liquid within the cells also starts to evaporate (the cells dry out).

The scraper used for the smearing may be hand-held and can be designed as a tube without sharp edges that may potentially damage the cells, e.g. a pipette tube used in the horizontal position.

The tube used for aspirating cells from the surface may advantageously be designed in a certain manner so that it has a valve function. When the selected cell has been aspirated into the tube, this same cell acts as a ball in a ball valve. This means that the cell, when in place, will close the tube for further flow ensuring that no further cells are unintentionally aspirated, i.e. non-selected cells.

For many reasons, the preparation process before the cell mass is laid out on the disc is arranged so that it is treating the cell mass as gently as possible. This is done in order to minimize the loss of cells during the process before scanning. The cells which are often most fragile will often be the target cells it is desired to find, e.g. circulating cancer cells. Therefore a gentle process is important. The gentle process i.a. comprises that the number of washing processes is minimized, including centrifugations and rinsing with clean carrier liquid. The washing steps are therefore fewer than by common instructions for fluorescence colouring processes. However, an important side effect is that the carrier liquid used when the cell mass is spread over the glass disc (laying out) will contain a residual amount of serum. This serum contributes to the protection of the cells against complete drying out when they are dried on the glass surface. A sort of film is formed (rubber-like film) over the cells which will normally be considered to be undesired, but in this case it is desirable in order not to cause complete drying out and thus too strong attachment to the surface.

When collecting a selected cell on the surface, it is preferred that the operator is able to see the target cell on the one hand and on the other hand the surrounding cells and also the tube (used for pushing the cell and aspirating the cell). In one embodiment of the presently disclosed apparatus a light source is placed next to the tube so that it is illuminated and thus becomes visible in the microscope, even when the microscope has been set in a certain fluorescence mode, as the light on/in the tube is scattered broadly in all frequency bands.

The present disclosure further relates to method for preparing a manipulation medium such that one or more object(s) can be detected and manipulated, said method comprising the steps of:
   providing the object(s), said object(s) being contained in a carrier liquid;
   spreading the carrier liquid on the manipulation medium;
   starting a process of drying the carrier liquid; and
   stopping the process of drying the carrying liquid, thereby creating a loose bond between the object(s) and the manipulation medium
and to a method for detection and manipulation of one or more objects, said method comprising the steps of:
   placing a manipulation medium prepared according to the method for preparing a manipulation medium into an apparatus as described above;
   detecting at least one object by means of the microscope; and
   manipulating at least one object by observing the at least one object and the tube in the microscope such that the tube moves and/or pushes the object.

In the method for preparing a manipulation medium, the step of spreading the carrier liquid may be a smearing process.

The method for detection and manipulation of one or more objects may comprise an analysis of the at least one object in the step of detecting at least one object. The step of manipulating at least one object may be carried out by the control unit via input from a vision system coupled to the microscope. Furthermore the method may involve a transfer of the object(s) by moving them to an isolation medium by means of the tube. The transfer step may be carried out by the control unit via input from a vision system coupled to the microscope.

DETAILED DESCRIPTION OF THE DRAWINGS

The invention will in the following be described in greater detail with reference to the accompanying drawings. The drawings are exemplary and are intended to illustrate some of the features of the presently disclosed method for attaching, detecting and retrieving a single cell on a manipulation medium and apparatus for detection and manipulation of one or more objects, and are not to be construed as limiting to the presently disclosed invention.

FIG. 1 shows one embodiment of a tube (4) for aspirating a single cell (5) from a manipulation medium (1). The tube (4) may also be used to loosen a single cell (5) from the manipulation medium (1). In the example, the single cell (5) is situated among non-selected cells (2) in a carrier liquid (3). The tip of the tube (4) may be used to loosen the single cell (5) e.g. by gently pushing and rubbing the single cell (5) in a controlled manner. The liquid (3) covering the cells may assist the tube (4) in lifting the single cell (5) from the manipulation medium (1) into the tube (4). When the cell is in the tube (4), it acts as a sort of ball valve stopping the liquid flow and thus preventing further cells from being aspirated. For this purpose, in the example, the tube (4) has a proximal section (8) having a width of at least the diameter of the single cell (5) and a middle section (6) abutting the proximal section (8), wherein the middle section (6) is narrower than the diameter of the single cell (5). The tube (4) of FIG. 1 also has a distal section (7), which is wider than the middle section (6).

Figure 2:
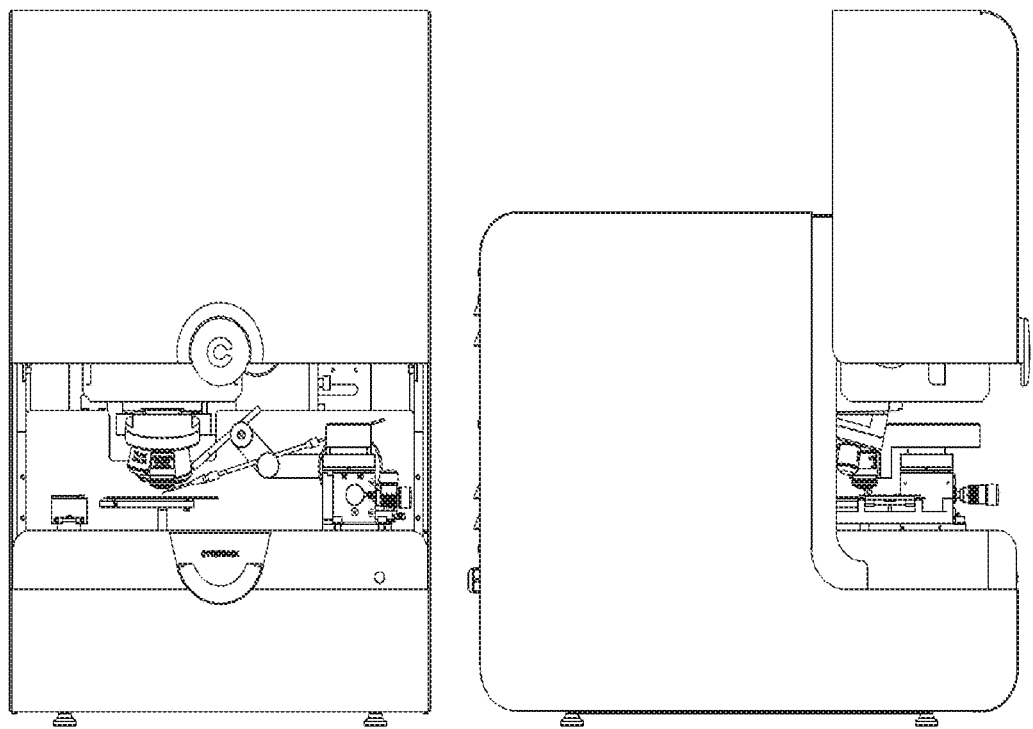
FIG. 2 shows one embodiment of an apparatus for detection and manipulation of one or more objects.
Figure 3:
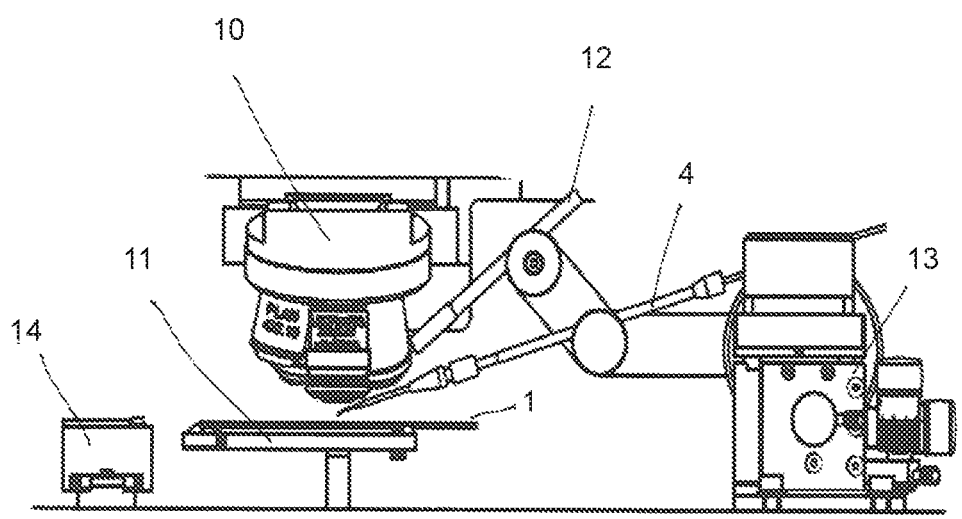
FIG. 3 shows a further embodiment of an apparatus for detection and manipulation of one or more objects.

FIG. 2 shows one embodiment of an apparatus for detection and manipulation of one or more objects. The apparatus has a micromanipulation system comprising a control unit, an arm adapted for holding a tube, wherein the tube is adapted to be moved in one or more directions following instructions from the control unit, and a microscope having a field of view, FIG. 3 shows a a further embodiment of an apparatus for detection and manipulation of one or more objects The apparatus has an optical system (10), typically a fluorescence microscope, a clamp (11) holding a glass disc (1), partly for rotation, partly for linear movement, onto which a cell mass has been laid out and in which the cells are partly attached to the surface in a layer, a pipette tube (4) used partly for pushing the cells to be isolated, partly for aspirating the cells, micromanipulation system (13) that can move the pipette tube (4) in three dimensions, a lamp (12) which can illuminate the pipette tube (4) such that it becomes visible in the microscope, and a device (14) which can hold one or more Eppendorf tubes and/or one or more microscope slides. This device (14) can be mechanically coupled to the clamp (11) such that the same movement system can perform both functions, which provides a simpler and cheaper system.

Figure 4:
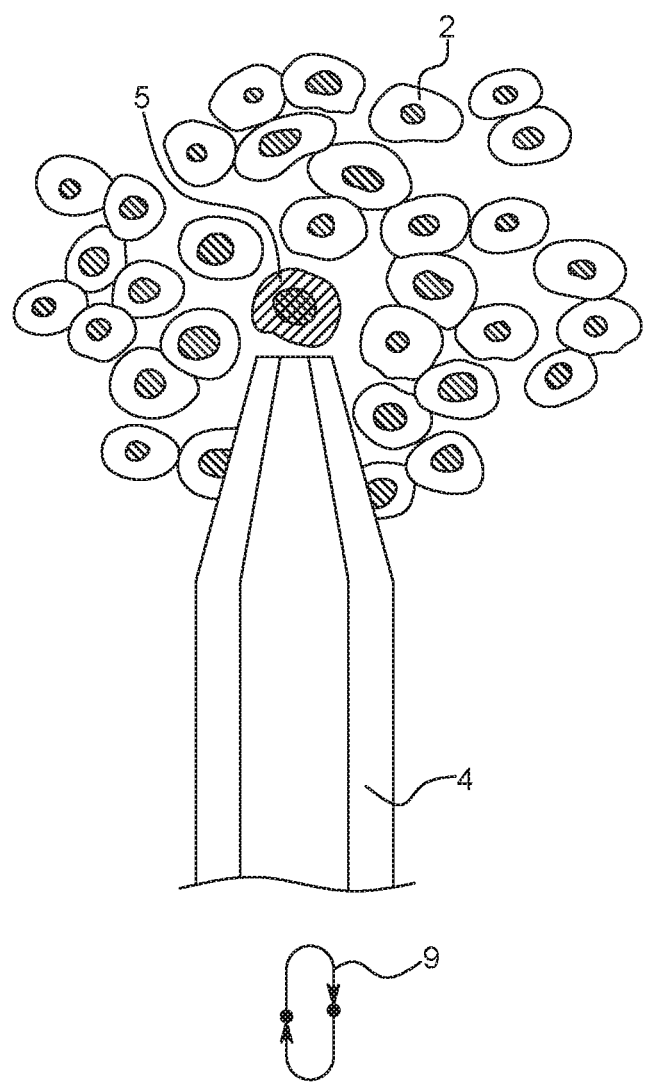
FIG. 4 shows one embodiment of a tube loosening a single cell from a manipulation medium and for aspirating the single cell.

FIG. 4 shows one embodiment of a tube (4) loosening a single cell (5) from a manipulation medium (not shown) and for aspirating the single cell (5), wherein the tube (4) is used to push the target cell (5) loose and aspirate the cell (5). The single cell (5) is situated among a number of background cells (2). The single cell (5) and the background cells (2) are fluorescently labelled with different colours. The operator pushes the target cell loose with small movements (9), as illustrated.

The invention claimed is:

1. A method for attaching, detecting and retrieving a single cell on a manipulation medium comprising the steps of:
   attaching the single cell onto the manipulation medium by applying a carrier liquid;
   partially drying out the carrier liquid;
   detecting a property of the single cell by rotating the manipulation medium and scanning a light beam over the manipulation medium;
   loosening the single cell from the manipulation medium without damaging the single cell by manipulating the single cell with an instrument; and
   retrieving the single cell from the manipulation medium by aspirating the single cell into a tube,
wherein the carrier liquid is dried out to a degree corresponding to that the single cell does not move during the rotation of the manipulation medium and that the single cell can be loosened by the instrument without damaging the single cell.

2. The method according to claim 1, wherein the carrier liquid is a coating.

3. The method according to claim 2, wherein the coating is selected from the group of Poly-L-Lysin or SuperFrost.

4. The method according to claim 1, wherein the single cell is exposed to centrifugal forces, translational forces or gravitational forces during rotation of the manipulation medium.

5. The method according to claim 1, wherein the single cell is loosened by pushing or rubbing the single cell with the instrument.

6. The method according to claim 1, wherein the instrument is moved in a controlled movement to push or rub the single cell loose.

7. The method according to claim 1, further comprising the step of applying additional liquid to an area on and/or around the single cell to dissolve bonds fixing the single cell.

8. The method according to claim 7, wherein the additional liquid is water, an oil or phosphate-buffered saline (PBS).

9. The method according to claim 1, wherein the step of detecting a property of the single cell further comprises the step of detecting light emitted from the single cell.

10. The method according to claim 1, wherein the single cell is loosened by the tip of the instrument.

11. The method according to claim 1, wherein the single cell is pushed or rubbed with the tip of the instrument.

12. The method according to claim 1, wherein the instrument for pushing or rubbing the cell loose is a tube.

* * * * *